United States Patent [19]

Kappl et al.

[11] Patent Number: 4,516,459
[45] Date of Patent: May 14, 1985

[54] DRIVE-CONTROL SYSTEM FOR A MICROTOME, IN PARTICULAR AN ULTRAMICROTOME

[75] Inventors: Gerhard Kappl; Helmut Kranner; Reinhard Lihl, all of Vienna, Austria

[73] Assignee: C. Reichert Optische Werke, Vienna, Austria

[21] Appl. No.: 512,098

[22] Filed: Jul. 8, 1983

[51] Int. Cl.³ .............................................. B26D 7/06
[52] U.S. Cl. ........................................ 83/713; 83/412; 83/915.5; 83/717
[58] Field of Search ................... 83/915.5, 412–414, 83/713, 717

[56] References Cited

U.S. PATENT DOCUMENTS 3,293,972 12/1966 Burkhardt ............................ 83/414
3,845,659 11/1974 Wikefeldt ........................... 83/915.5
4,126,069 11/1978 Shimonaka ............................ 83/703

Primary Examiner—James M. Meister
Assistant Examiner—John L. Knoble
Attorney, Agent, or Firm—Alan H. Spencer; Stephen Raines

[57] ABSTRACT

A microtome, in particular an ultramicrotome, has a drive-control system by which the movement of the specimen arm, relative to the knife, is subdivided into a comparatively slow cutting movement and a more rapid return movement. The drive-control system gradually decelerates the specimen arm at the transition, from the comparatively rapid return movement to the slower cutting movement, so that a jerk, which would generate mechanical vibrations in the drive system, is avoided and the specimen arm is smoothly decelerated from the comparatively high speed to the lower speed.

7 Claims, 3 Drawing Figures

DRIVE-CONTROL SYSTEM FOR A MICROTOME, IN PARTICULAR AN ULTRAMICROTOME

BACKGROUND OF THE INVENTION

The invention relates to a microtome, in particular, an ultramicrotome.

In a known microtome, for example, that disclosed in West German Pat. No. 2,246,853, a specimen arm can be used to execute an oscillating-stroke movement by means of an electric-drive motor and crank mechanism. A drive-control system for the drive motor subdivides the stroke movement of the specimen arm into a comparatively slow-cutting movement, during which the specimen arm is guided past a knife to produce a thin section of the specimen present on the arm, and a more rapid return movement, during which the specimen arm is guided back, outside the knife, into its starting position.

As a rule, microtomes of the abovementioned type have a direct-current drive motor, coupled to a tachometer generator, and the motor drives the crank of the specimen arm via a drive belt and pulley which serves as a flywheel. The subdivision into a comparatively slow-cutting movement and a rapid return movement is effected in order to return the specimen arm, as rapidly as possible, to its starting position, following the cutting movement which is appropriately adjusted so as to produce optimum thin sections, this mode of operation being embodied in the interests of time saving. The two movements are controlled by reducing the control voltage appropriately at the transition from the comparatively rapid movement to the slower movement, and increasing the control voltage again at the transition to the more rapid movement.

Since, in order to achieve isolation from externally imposed disturbances caused by vibration, the drive mechanisms of microtomes, and especially of ultramicrotomes, incorporate resilient elements, the drive shaft of the drive motor starts to oscillate during the above-mentioned speed change which causes the belt drive and the flywheel to vibrate as well. In such a case, the drive motor, which is controlled by means of the tachometer generator, can also be induced to resonate by the tachometer generator. Vibrations of this nature are, however, disadvantageous because they correspondingly manifest themselves in a vibratory movement of the specimen arm, this movement having an adverse effect on the quality of the thin section which is to be produced. In the case of the known microtomes, it is accordingly necessary to set the change-over from the comparatively-rapid return movement to the slower-cutting movement at a point in time which is sufficiently in advance of the start of the actual cutting operation to ensure that the vibrations, generated in the mechanical-drive system by the speed-change jerk, have already died away. This, however, reduces the rate at which the microtome operates.

OBJECT OF THE INVENTION

An object of the invention is to provide a drive-control system for a microtome, which system enables the change-over from the rapid-return movement to the slower-cutting movement to be set at a point in time immediately in advance of the actual cutting operation without the generation of disadvantageous vibrations in the mechanical-drive system which adversely affect the quality of the thin section to be produced.

BRIEF DESCRIPTION OF THE INVENTION

According to the invention there is provided a microtome comprising a specimen arm for holding a specimen, a knife positioned adjacent to said arm, drive means comprising an electric-drive motor, and a crank mechanism for moving said arm in an oscillating-stroke movement, said stroke movement comprising a cutting movement in which a specimen on said arm is passed from a starting position over said knife to produce a thin section of said specimen and a return movement in which said specimen is returned to said starting position along a path spaced from said knife, and a drive-control system for varying the speed of said motor such that said return movement of said arm is substantially faster than said cutting movement, said drive-control system being adapted to decelerate said specimen arm gradually at the transition from said return movement to said cutting movement.

In a microtome of the invention, the change-over from the comparatively-high value of the control voltage to the lower-voltage value is not effected abruptly, as hitherto, but the voltage is gradually reduced to its lower value in a manner such that the deceleration resulting from this voltage reduction does not induce mechanical vibrations in the drive system. Most advantageously, the voltage reduction, and the accompanying voltage profile, are adjusted to induce the damping, which is inherent in the mechanical-drive system, to give rise to an aperiodic change in the movement of the specimen arm between the comparatively-rapid movement and the slower movement (critical damping), during which variation the specimen arm is prevented from executing a transient movement in the direction opposite to the cutting direction.

It has proved particularly advantageous to impose a linear profile on the control voltage between its higher and lower values. According to a special embodiment of the drive-control system, this linear profile can be achieved by incorporating in the drive-control system a constant-current source and a capacitor which is to be charged by the constant-current source, or which is to be discharged, as the case may be.

By arranging for the electrical and/or electronic elements influencing the control-voltage profile to be variable, it is possible to bring about a vibration-free transition from the comparatively-rapid movement of the specimen arm to its slower movement for every cutting speed which can be set. In each case, this procedure involves adjusting the control-voltage profile in such a manner as to establish the abovementioned aperiodic change in the movement.

BRIEF DESCRIPTION OF THE DRAWINGS

Further advantages and features of the present invention are evident from the following description of an illustrative embodiment, which description refers to the drawings in which.

DETAILED DESCRIPTION OF THE INVENTION

Figure 1:
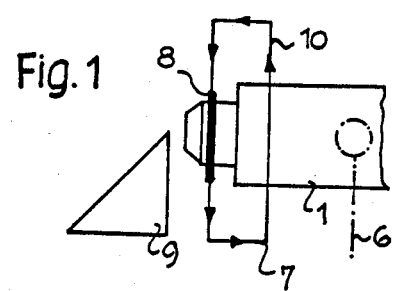
FIG. 1 is a diagrammatic representation of the movement of the specimen arm of an ultramicrotome.
Figure 2:
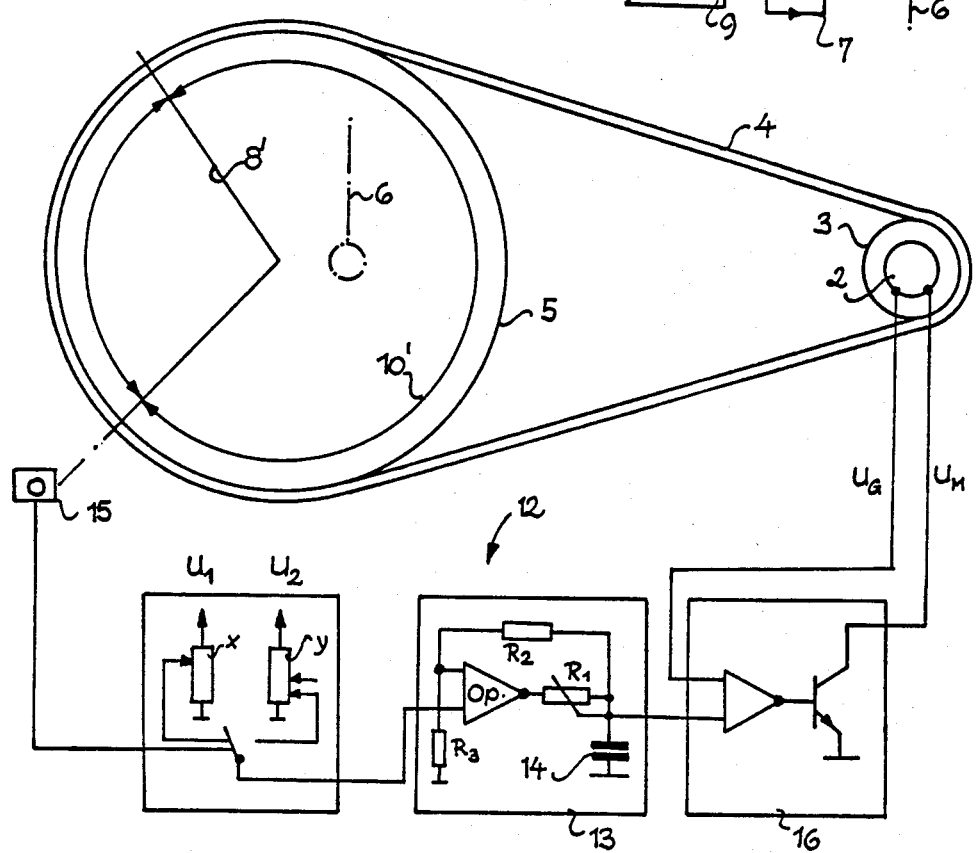
FIG. 2 is a diagrammatic representation of the drive system for the specimen arm, according to FIG. 1, and of the drive-control system according to the invention.

FIG. 1, and the upper portion of FIG. 2, show diagrammatically the front end of a specimen arm 1 of an ultramicrotome and the drive system for the specimen arm 1, the ultramicrotome not being shown in its entirety. This drive system comprises, in a known manner, an electric-drive motor 2 which is of the direct-current type and is controlled to run at a constant speed by means of a tachometer generator, which is not shown, a belt pulley 3, a belt 4, and a flywheel 5, the latter serving at the same time as a belt pulley. The connection 6, between the flywheel 5 and the specimen arm 1, is effected by means of a crank mechanism, and is not shown in detail. To this extent, the mechanical construction of the ultramicrotome does not differ from that of known ultramicrotomes, for example, that disclosed in West German Pat. No. 2,246,853.

The specimen arm 1 is guided, by means of devices which are not represented in detail, in the course of its upward and downward movement, along a closed-movement path 7. Within this path 7, the arm 1 executes a cutting movement 8 during which the cutting edge of a knife 9 produces a thin section from the specimen held thereby. In this respect, the specimen arm is of conventional form and the mounting of the specimen is, therefore, not shown in more detail. The cutting movement 8 is represented by a heavy line, and is followed by a rapid-return movement 10, represented by a thin line. In FIG. 2, the sector 8′ of one rotation of the flywheel 5 represents that portion of the movement path which corresponds to the cutting movement 8, while the return movement 10 is represented by the sector 10′ of one rotation of the flywheel.

Figure 3:
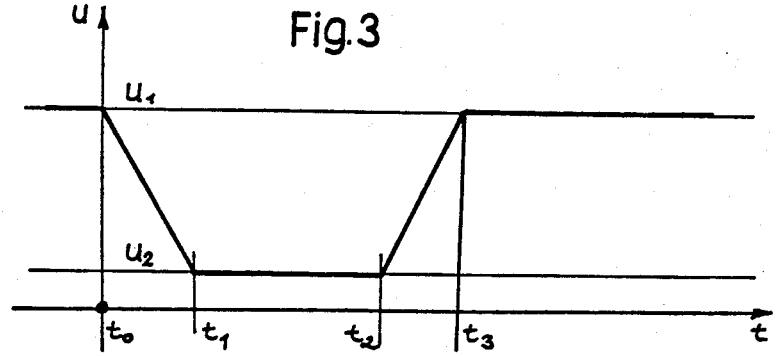
FIG. 3 is a graph which displays the profile according to which the control voltage is varied, this voltage being applied to the drive motor by the drive-control system according to the invention.

As can be seen from FIG. 3, the control voltage U which is to be applied to the drive motor 2 is now controlled, according to the invention, in a manner such that a higher control voltage $U_1$ is applied to the drive motor 2 during the comparatively-rapid return movement 10, and a lower-control voltage $U_2$ is applied during the comparatively-slow cutting movement 8, while at the transition between the two movements, 8 and 10, the control voltage U rises following a linear profile during the time interval $t_2$–$t_3$ or, as the case may be, falls, likewise following a linear profile during the time interval $t_0$–$t_1$. The rate of rise or, as the case may be, the rate of fall of this linear-voltage profile is adjusted, as hereinbefore described, in a manner such that a vibration-free transition from one movement to the other is established in the drive system.

The lower portion of FIG. 2 shows a circuit diagram for the electronic-control module 12, by means of which it is possible to achieve the control-voltage profile according to the invention, shown in FIG. 3. The electronic-control module 12 incorporates a constant-current source for supplying the drive motor 2 and a capacitor 14 of capacitance C. The electronic-control module 12 can set the drive motor 2 to two alternate switching states, indicated by $U_1$ and $U_2$.

The constant-current source 13 supplies a constant current $i_c$, so that a voltage change occurring over a finite time, dU/dt, follows the known relationship:

$$dU/dt = i_c \cdot 1/C$$

From this relationship, the voltage change U(t) during the time t between the control voltages $U_1$ and $U_2$ is given by $$U(t) = i_c/C \cdot t.$$

The rate of rise, or fall, of the voltage profile during the time t can be fixed by appropriately adjusting the constant current $i_c$, and/or the capacitance C of the capacitor 14.

In order to preselect the speed of the drive motor 2, two potentiometers, x and y, are alternately connected to the constant-current source 13 by means of a light-activated switch 15. The light-activated switch 15 controls the sector 8′ for the cutting movement 8 or the sector 10′ for the return movement 10, and is, for example, activated by means of a screen which is attached to the flywheel 5, but which is not shown. The electrical signal from the potentiometer x or, as the case may be, y is supplied to an operational amplifier Op which acts as an impedance converter and constant-current source. The amplification factor is determined by the resistor $R_2$, and the current $i_c$ for charging the capacitor 14 is determined by the resistor $R_1$. The voltage applied to the capacitor 14 is now supplied to a series-connected comparator and power-output stage 16 for supplying the drive motor 2. The comparator and power-output stage 16 receives the voltage $U_G$ from the tachometer generator on the drive motor 2, this voltage, which is an analog of the rotational speed of the drive motor 2, being supplied via a separate line $U_G$. The supply voltage for the drive motor 2 is indicated by $U_M$.

We claim:

1. A rotary driven microtome having a control to dissipate vibrations prior to cutting a specimen, which comprise a specimen arm for holding a specimen, a knife positioned adjacent to said arm, drive means comprising an electric drive motor and a crank mechanism for moving said arm in an oscillating stroke movement, said stroke movement comprising a cutting movement in which a specimen on said arm is passed from a starting position over said knife to produce a thin section of said specimen and a return movement in which said specimen is returned near to said starting position along a path spaced from said knife, and a motor-control system for varying the speed of said electric motor, a cutting signal generated by said control system, a return signal generated by said control system and a transition signal generated by said control system, said transition signal controlling deceleration of said specimen arm to dissipate vibrations prior to the cutting movement.

2. The microtome according to claim 1 wherein the speed of said electric motor is controlled by signal voltage.

3. The microtome according to claim 2 wherein the signal voltages are adjustable.

4. The microtome according to claim 2 wherein said deceleration signal decreases linearly.

5. The microtome according to claim 2 further including an acceleration signal.

6. The microtome according to claim 2 wherein said control system includes a constant current source.

7. The microtome according to claim 5 wherein said control system includes a constant current source and a capacitor, said capacitor controlling said deceleration and acceleration signals.

* * * * *